United States Patent
Jäkel et al.

(10) Patent No.: US 7,534,921 B2
(45) Date of Patent: May 19, 2009

(54) METHOD FOR THE PRODUCTION OF OPTICALLY ACTIVE CARBONYL

(75) Inventors: Christoph Jäkel, Limburgerhof (DE); Rocco Paciello, Bad Dürkheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 89 days.

(21) Appl. No.: 11/577,068

(22) PCT Filed: Oct. 8, 2005

(86) PCT No.: PCT/EP2005/010847

§ 371 (c)(1), (2), (4) Date: Apr. 11, 2007

(87) PCT Pub. No.: WO2006/040096

PCT Pub. Date: Apr. 20, 2006

(65) Prior Publication Data

US 2008/0269528 A1    Oct. 30, 2008

(30) Foreign Application Priority Data

Oct. 11, 2004    (DE)    ........................ 10 2004 049 631

(51) Int. Cl.
C07C 45/62    (2006.01)
(52) U.S. Cl. ...................... 568/408; 568/457
(58) Field of Classification Search .................. 568/408, 568/459

See application file for complete search history.

(56) References Cited

U.S. PATENT DOCUMENTS 4,237,072 A    12/1980    Aviron-Violet et al.

FOREIGN PATENT DOCUMENTS

| EP | 0 000 315 A1 | 1/1979 |
|---|---|---|
| EP | 1 053 974 A1 | 11/2000 |
| EP | 1 225 163 | 7/2002 |
| JP | 52-78812 | 7/1977 |

OTHER PUBLICATIONS

Dang et al., "Catalyse d'hydrogenation en phase homogene des aldehydes α-β insatures: application a la synthese asymetrique du citronellal," J. Mol. Cat., 1982, vol. 16, pp. 51-59.

Chapuis et al., "Synthesis of citronellal by Rh$^I$—catalysed asymmetric isomerization of N, N-diethyl-substituted geranyl- and nerylamines or geraniol and nerol inthe presence of chiral diphosphino ligands, under homogeneous ans supported conditions," Helvetica Chimica Acta, 2001, vol. 84, pp. 230-242.

Tang et al., "New chiral phosphorus ligands for enantioselective hydrogenation," Chem. Rev., 2003, vol. 103, pp. 3029-3069.

"Saturated aldehydes selective prodn.—by treating unsaturated aldehyde with hydrogen and carbon monoxide, using catalyst, tertiary phosphine and amine" WPI/DERWENT Database, Accession No. 1977-58267Y.

*Primary Examiner*—Sikarl A Witherspoon
(74) *Attorney, Agent, or Firm*—Connolly Bove Lodge & Hutz LLP

(57) ABSTRACT

The present invention relates to a process for preparing optically active carbonyl compounds by asymmetrically hydrogenating α,β-unsaturated carbonyl compounds in the presence of optically active transition metal catalysts which are soluble in the reaction mixture and have at least one carbon monoxide ligand. The present invention especially relates to a process for preparing optically active aldehydes or ketones, in particular citronellal, by asymmetrically hydrogenating the corresponding optically active α,β-unsaturated aldehydes or ketones.

20 Claims, No Drawings

METHOD FOR THE PRODUCTION OF OPTICALLY ACTIVE CARBONYL

RELATED APPLICATIONS

This application is a national stage application (under 35 U.S.C. 371) of PCT/EP2005/010847 filed Oct. 8, 2005, which claims benefit of German application 10 2004 049 631.5 filed Oct. 11, 2004.

The present invention relates to a process for preparing optically active carbonyl compounds by asymmetrically hydrogenating $\alpha,\beta$-unsaturated carbonyl compounds in the presence of optically active transition metal catalysts which are soluble in the reaction mixture and have at least one carbon monoxide ligand. The present invention especially relates to a process for preparing optically active aldehydes or ketones, in particular citronellal, by asymmetrically hydrogenating the corresponding optically active $\alpha,\beta$-unsaturated aldehydes or ketones.

Many optically active aldehydes and ketones constitute valuable intermediates for the synthesis of highly upgraded chiral substances of value and active ingredients, and are themselves often valuable fragrances and aromas.

EP-A 0 000 315 relates to a process for preparing optically active citronellal by hydrogenating geranial or neral in the presence of a catalyst complex which is dissolved in the reaction system and is composed of rhodium and a chiral phosphine.

In J. Mol. Cat. 1982, 16, 51-59, T.-P. Dang et al. describe the homogeneously catalyzed hydrogenation of $\alpha,\beta$-unsaturated aldehydes and the application of the process to the preparation of optically active citronellal. The catalysts used were complexes of a rhodium carbonyl and a chiral diphosphine.

In Helv. Chim. Acta 2001, 84, 230-242, footnote 4, Chapuis et al. also describe the asymmetric hydrogenation of geranial or neral to optically active citronellal in the presence of a catalyst composed of $Rh_4(CO)_{12}$ and (R,R)-chiraphos, (2R,3R)-2,3-bis(diphenylphosphino)butane.

A problem when carrying out reactions catalyzed (homogeneously) by means of soluble catalysts consists in the often insufficient stability of the catalyst complexes used or of the catalytically active metal or transition metal complex which forms therefrom. Against the background of the often high price of such catalysts or catalyst precursors, homogeneously catalyzed reactions with complex transition metal catalysts can be employed on the industrial scale in an economically viable manner only in specific cases.

JP-A 52078812 describes a process for hydrogenating $\alpha,\beta$-unsaturated aldehydes such as crotonaldehyde, cinnamaldehyde or $\alpha$-methylcinnamaldehyde over homogeneous Rh catalysts under hydroformylation conditions in the presence of a triarylphosphine, of a tertiary amine in a stoichiometric amount and of carbon monoxide.

It is an object of the present invention to provide a process for the homogeneously catalyzed asymmetric hydrogenation of $\alpha,\beta$-unsaturated aldehydes or ketones which is notable for increased stability and thus increased lifetime of the catalytically active transition metal complex to be used in optically active form, and is therefore suitable to a particular degree for applications on the industrial scale.

Surprisingly, this object is achieved by providing a process for preparing optically active carbonyl compounds by asymmetrically hydrogenating $\alpha,\beta$-unsaturated carbonyl compounds in the presence of optically active transition metal catalysts which are soluble in the reaction mixture and have at least one carbon monoxide ligand, which comprises pretreating the catalyst with a gas mixture comprising carbon monoxide and hydrogen and/or carrying out the asymmetric hydrogenation in the presence of carbon monoxide supplied additionally to the reaction mixture.

The process according to the invention is suitable for preparing optically active carbonyl compounds such as aldehydes, ketones, esters, lactones or lactams by asymmetrically, i.e. enantioselectively, hydrogenating the corresponding carbonyl compounds which have an ethylenic double bond in the $\alpha,\beta$-position relative to the carbonyl group. According to the invention, the ethylenic double bond in the $\alpha,\beta$-position relative to the carbonyl group is hydrogenated in the presence of an optically active transition metal catalyst which is soluble in the reaction mixture and has at least one carbon monoxide, i.e. CO, ligand to give a carbon-carbon single bond, the tetrahedral carbon atom which is newly created in the $\beta$-position being asymmetrically substituted and obtained in nonracemic form. Accordingly, the term asymmetric hydrogenation refers in the context of the present invention to a hydrogenation in which the two enantiomeric forms of the hydrogenation product are not obtained in equal parts. In the process according to the invention, the catalyst used which is soluble in the reaction mixture, i.e. homogeneous, is either pretreated before the asymmetric hydrogenation with a gas mixture which comprises carbon monoxide and hydrogen (i.e. what is known as a preformation), or the asymmetric hydrogenation is carried out in the presence of carbon monoxide supplied additionally to the reaction mixture, or a preformation is carried out and the asymmetric hydrogenation is subsequently carried out in the presence of carbon monoxide supplied additionally to the reaction mixture.

The transition metal catalysts which are soluble in the reaction mixture and are to be used in accordance with the present invention have at least one CO ligand at least in a form which is passed through in a catalytic cycle or in a form which precedes the actual catalytic cycle, but it is unimportant whether this catalyst form having at least one CO ligand constitutes the actual catalytically active catalyst form. In the context of the process according to the invention, the catalyst form having at least one CO ligand is stabilized in an advantageous manner by the carbon monoxide supplied additionally to the reaction mixture. It is especially surprising that carbon monoxide, known to be a catalyst poison, can also be used to promote the reaction to be carried out in accordance with the invention.

The process according to the invention is suitable to a particular degree for preparing optically active carbonyl compounds of the formula (I)

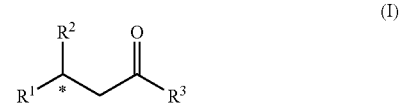

where
the $R^1$, $R^2$ radicals are each an unbranched, branched or cyclic alkyl radical which has from 1 to 25 carbon atoms and may optionally bear one or more, generally from 1 to about 5, ethylenic double bonds and/or one or more, generally from 1 to about 5, identical or different substituents selected from the group of the $OR^4$, $NR^5R^6$, halogen, $C_6$-$C_{10}$-aryl and $C_3$-$C_9$-hetaryl substituents and which, together with $R^3$, may form a 5- to 25-membered ring, with the proviso that $R^1$ and $R^2$ are different,
the $R^3$ radical is hydrogen or an unbranched, branched or cyclic alkyl radical which has from 1 to 25 carbon atoms and may optionally bear one or more, generally from 1 to about 5, ethylenic double bonds and/or one or more, generally from 1 to about 5, identical or different substituents selected from the group of the $OR^4$, $NR^5R^6$, halogen, $C_6$-$C_{10}$-aryl and $C_3$-$C_9$-hetaryl substituents, or is $OR^7$ or $NR^8R^9$, where $R^4$, $R^5$, $R^6$ are each independently hydrogen, $C_1$-$C_6$-alkyl, $C_6$-$C_{10}$-aryl, $C_7$-$C_{12}$-aralkyl or $C_7$-$C_{12}$-alkylaryl and $R^5$ and $R^6$ together may also be an alkylene chain having from 2 to 5 carbon atoms which may be interrupted by N or O and $R^7$, $R^8$ are each an unbranched, branched or cyclic alkyl radical which has from 1 to 25 carbon atoms and may optionally bear one or more, generally from 1 to about 5, ethylenic double bonds and/or one or more, generally from 1 to about 5, identical or different substituents selected from the group of the $OR^4$, $NR^5R^6$, halogen, $C_6$-$C_{10}$-aryl and $C_3$-$C_9$-hetaryl substituents, and, together with $R^1$ or $R^2$, may form a 5- to 25-membered ring and $R^9$ is hydrogen, $C_1$-$C_4$-alkyl, $C_6$-$C_{10}$-aryl, $C_7$-$C_{12}$-aralkyl or $C_7$-$C_2$-alkylaryl and \* indicates an asymmetric carbon atom, by asymmetrically hydrogenating α,β-unsaturated aldehydes or ketones of the formula (II)

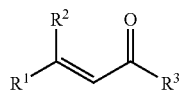

(II)

where the $R^1$ to $R^3$ radicals are each as defined above.

In the context of the present invention, the following definitions are specified by way of example for substituents or radicals mentioned:

$C_1$-$C_{10}$-Alkyl is, for example, methyl, ethyl, propyl, 1-methylethyl, butyl, 1-methylpropyl, 2-methylpropyl, 1,1-dimethylethyl, pentyt, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl or 1-ethyl-2-methylpropyl.

$C_6$-$C_{10}$-Aryl is, for example, phenyl or naphthyl.

$C_7$-$C_{12}$-Aralkyl is, for example, phenylmethyl, 1-phenylethyl, 2-phenylethyl, 1-phenylpropyl, 2-phenylpropyl or 3-phenylpropyl.

$C_3$-$C_9$-Hetaryl is, for example, 2-furyl, 3-furyl, 2-pyrroyl, 3-pyrroyl, 2-thienyl, 3-thienyl, 2-pyridyl, 3-pyridyl, 4-pyridyl, 2-indolyl, 3-indolyl, 4-indolyl, 5-indolyl, 6-indolyl, 7-indolyl.

$C_7$-$C_{12}$-Alkylaryl is, for example, 1-methylphenyl, 2-methylphenyl, 3-methylphenyl, 1-ethylphenyl, 2-ethylphenyl, 3-ethylphenyl, 1-propylphenyl, 2-propylphenyl, 3-propylphenyl, 1-isopropylphenyl, 2-isopropylphenyl, 3-isopropylphenyl, 1-butylphenyl, 2-butylphenyl, 3-butylphenyl, 1-isobutylphenyl, 2-isobutylphenyl, 3-isobutylphenyl, 1-sec-butylphenyl, 2-sec-butylphenyl, 3-sec-butylphenyl, 1-tert-butylphenyl, 2-tert-butylphenyl, 3-tert-butylphenyl, 1-(1-pentenyl)phenyl, 2-(1-pentenyl)phenyl, 3-(1-pentenyl)phenyl, 1-(2-pentenyl)phenyl, 2-(2-pentenyl)phenyl, 3-(2-pentenyl)phenyl, 1-(3-pentenyl)phenyl, 2-(3-pentenyl)phenyl, 3-(3-pentenyl)phenyl, 1-(1-(2-methylbutyl))phenyl, 2-(1-(2-methylbutyl))phenyl, 3-(1-(2-methylbutyl))phenyl, 1-(2-(2-methylbutyl))phenyl, 2-(2-(2-methylbutyl))phenyl, 3-(2-(2-methylbutyl))phenyl, 1-(3-(2-methylbutyl))phenyl, 2-(3-(2-methylbutyl))phenyl, 3-(3-(2-methylbutyl))phenyl, 1-(4-(2-methylbutyl))phenyl, 2-(4-(2-methylbutyl))phenyl, 3-(4-(2-methylbutyl))phenyl, 1-(1-(2,2-dimethylpropyl))phenyl, 2-(1-(2,2-dimethylpropyl))phenyl, 3-(1-(2,2-dimethylpropyl))phenyl, 1-(1-hexenyl)phenyl, 2-(1-hexenyl)phenyl, 3-(1-hexenyl)phenyl, 1-(2-hexenyl)phenyl, 2-(2-hexenyl)phenyl, 3-(2-hexenyl)phenyl, 1-(3-hexenyl)phenyl, 2-(3-hexenyl)phenyl, 3-(3-hexenyl)phenyl, 1-(1-(2-methylpentenyl))phenyl, 2-(1-(2-methylpentenyl))phenyl, 3-(1-(2-methylpentenyl))phenyl, 1-(2-(2-methylpentenyl))phenyl, 2-(2-(2-methylpentenyl))phenyl, 3-(2-(2-methylpentenyl))phenyl, 1-(3-(2-methylpentenyl))phenyl, 2-(3-(2-methylpentenyl))phenyl, 3-(3-(2-methylpentenyl))phenyl, 1-(4-(2-methylpentenyl))phenyl, 2-(4-(2-methylpentenyl))phenyl, 3-(4-(2-methylpentenyl))phenyl, 1-(5-(2-methylpentenyl))phenyl, 2-(5-(2-methylpentenyl))phenyl, 3-(5-(2-methylpentenyl))phenyl, 1-(1-(2,2-dimethylbutenyl))phenyl, 2-(1-(2,2-dimethylbutenyl))phenyl, 3-(1-(2,2-dimethylbutenyl))phenyl, 1-(3-(2,2-dimethylbutenyl))phenyl, 2-(3-(2,2-dimethylbutenyl))phenyl, 3-(3-(2,2-dimethylbutenyl))phenyl, 1-(4-(2,2-dimethylbutenyl))phenyl, 2-(4-(2,2-dimethylbutenyl))phenyl, 3-(4-(2,2-dimethylbutenyl))phenyl.

In the context of the present invention, halogen refers to fluorine, chlorine, bromine or iodine, preferably fluorine, chlorine or bromine.

The process according to the invention is accordingly suitable, for example, for preparing the following compounds of the formulae (I-1) to (I-25) specified by way of example in optically active form:

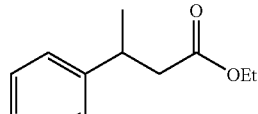

(I-1)

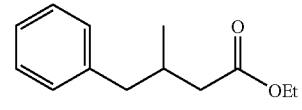

(I-2)

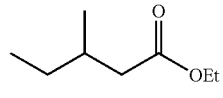

(I-3)

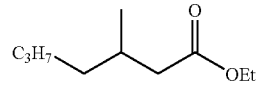

(I-4)

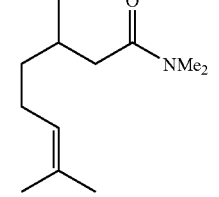

(I-5)

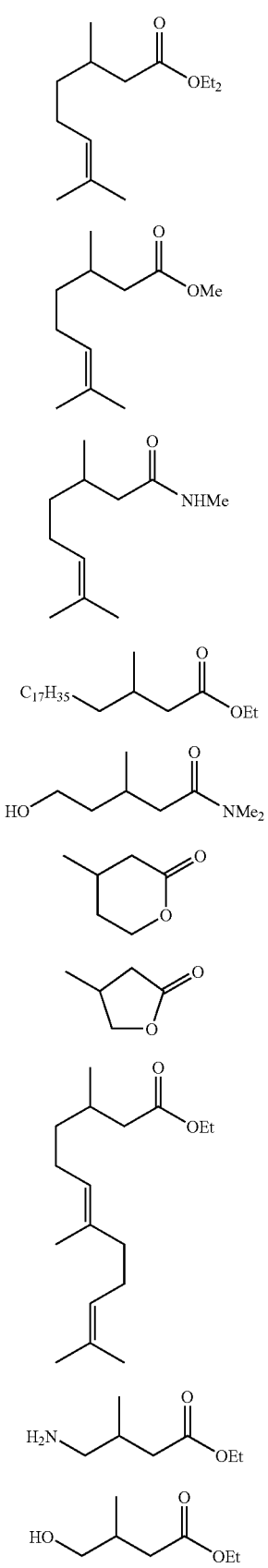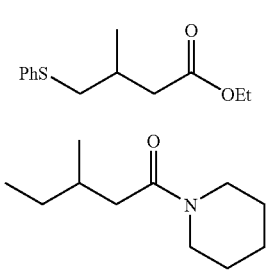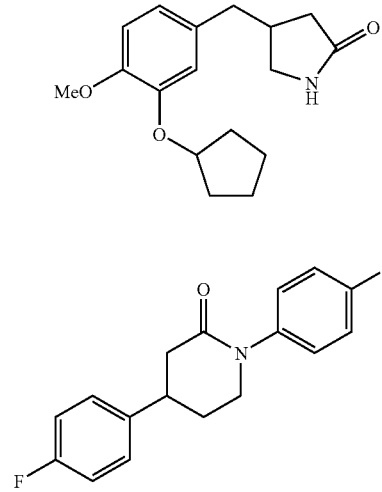

-continued

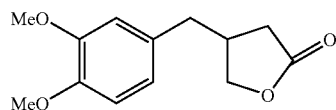
(I-25)

The process according to the invention is especially suitable for preparing optically active aldehydes or ketones by asymmetrically hydrogenating α,β-unsaturated aldehydes or ketones. Accordingly, it is especially suitable for preparing optically active compounds of the formula (I')

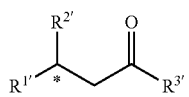
(I')

in which $R^{1'}$, $R^{2'}$ may each be as defined above for $R^1$ and $R^2$ and $R^{3'}$ is hydrogen or an unbranched, branched or cyclic alkyl radical which has from 1 to 25 carbon atoms and may optionally bear one or more, generally from 1 to about 5, ethylenic double bonds and/or one or more, generally from 1 to about 5, identical or different substituents selected from the group of the $OR^4$, $NR^5R^6$, halogen, $C_6$-$C_{10}$-aryl and $C_3$-$C_9$-hetaryl substituents, where $R^4$, $R^5$ and $R^6$ may each be as defined above, by asymmetrically hydrogenating α,β-unsaturated aldehydes or ketones of the formula (II')

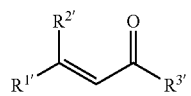
(II')

where the $R^{1'}$ to $R^{3'}$ radicals are each as defined above.

The process according to the invention is preferentially suitable for preparing optically active aldehydes of the formula (III) which have a methyl group in the β-position relative to the carbonyl group

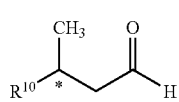
(III)

where $R^{10}$ is an unbranched or branched alkyl radical which has from 2 to 25 carbon atoms and may optionally have from 1 to 5 ethylenic double bonds and

* indicates an asymmetric carbon atom, by asymmetrically hydrogenating α,β-unsaturated aldehydes of the formula (IV) or (V)

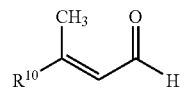
(IV)

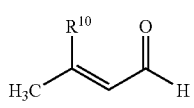
(V)

where the $R^{10}$ radical is as defined above.

Examples of aldehydes or ketones of the formulae (I') or (III) which can be prepared in optically active form in accordance with the invention include the following compounds:

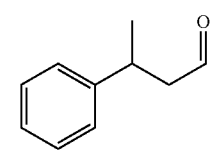
(I'-1)

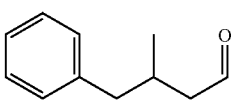
(I'-2)

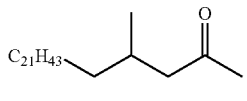
(I'-3)

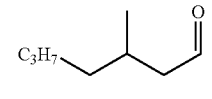
(III-1)

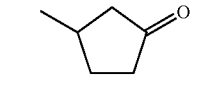
(I'-4)

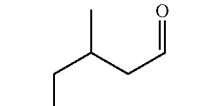
(III-2)

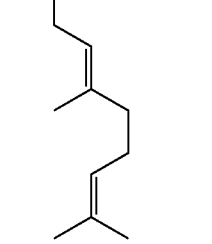
(III-4)

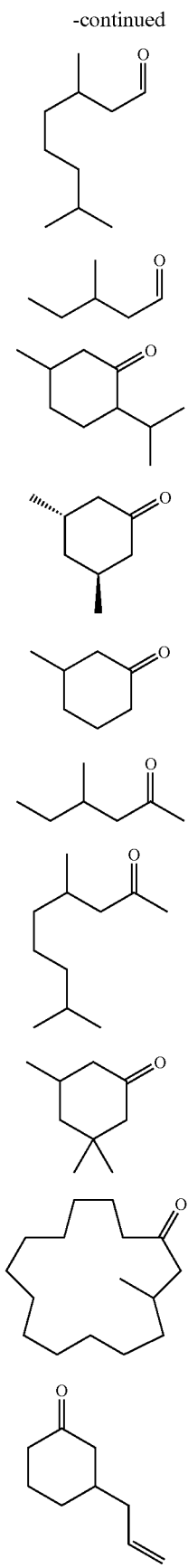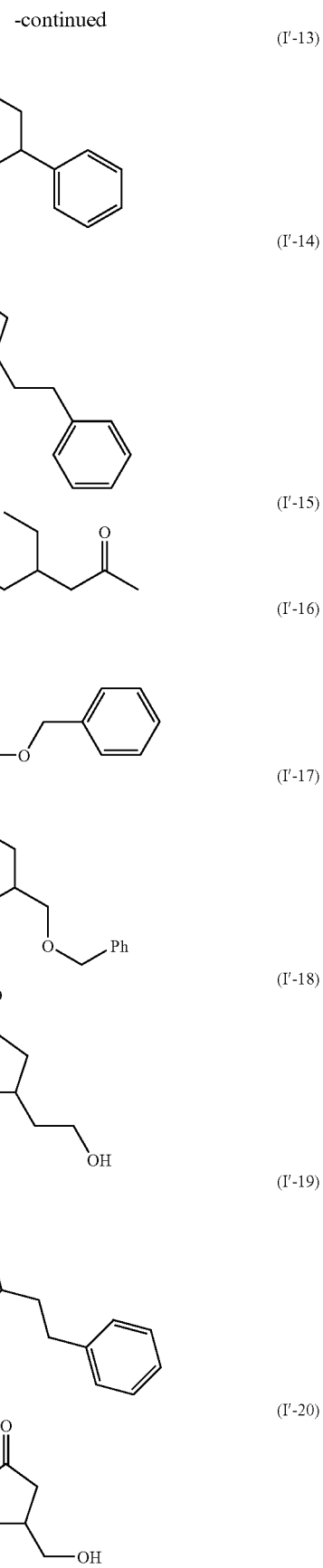

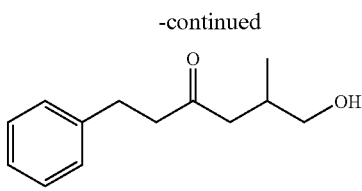
(I'-21)

According to the invention, the aldehydes of the formula (III) are accessible by asymmetrically, i.e. enantioselectively, hydrogenating the corresponding α,β-unsaturated aldehydes of the formulae (IV) or (V). The compounds of the formulae (IV) and (V) constitute E/Z-double bond isomers of one another. In principle, the optically active aldehydes of the formula (Ill) are accessible starting from both double bond isomers of the formulae (IV) and (V). Depending on the selection of the enantiomeric form of the catalyst, i.e. depending on the selection of the (+)- or (−)-enantiomer of the catalyst and of the (+)- or (−)-enantiomer of the chiral ligand used, one of the enantiomers of the optically active aldehyde is obtained preferentially in the inventive manner from the E- or Z-double bond isomer used. The same applies to the aforementioned substrate or product classes. In principle, it is also possible to convert mixtures of the two double bond isomers in the inventive manner. In this way, mixtures of the two enantiomers of the desired target compound are obtained.

The process according to the invention is more preferentially suitable for preparing optically active citronellal of the formula (VI)

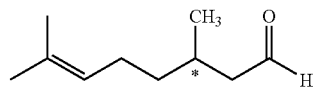
(VI)

by asymmetrically hydrogenating neral of the formula (VII) or geranial of the formula (VIII)

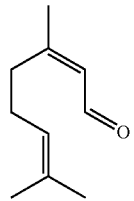
(VII)

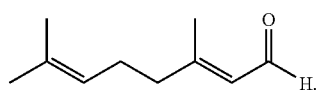
(VIII)

It is also possible to convert mixtures of geranial and neral in the inventive manner, in which case, as described above, mixtures of D- and L-citronellal are present and are optically active if the two enantiomers are not present therein in equal parts.

Especially preferred in the process according to the invention is the inventive preparation of D-citronellal by asymmetric hydrogenation of neral or geranial.

The inventive preparation process is carried out in the presence of an optically active transition metal catalyst which is soluble in the reaction mixture and has at least one carbon monoxide ligand.

Such catalysts are, for example, obtainable by reaction of at least one suitable transition metal compound which is soluble in the reaction mixture with an optically active ligand which has at least one phosphorus and/or arsenic atom.

Preferred transition metal compounds are those of the metals of transition group VIII of the Periodic Table of the Elements, in particular Ru, Rh, Pd, Ir and Pt. Transition metals of transition group VIII of the Periodic Table which are particularly preferred in accordance with the invention are Rh and Ir.

Suitable compounds of the transition metals mentioned are in particular those which are soluble in the selected reaction medium, for example salts or complexes with suitable ligands, for example carbonyl, acetylacetonate, hydroxyl, cyclooctadiene, norbornadiene, cyclooctene, methoxy, acetyl or other aliphatic or aromatic carboxylates. Transition metal compounds which are preferred in the process according to the invention are Rh(I) and Rh(III) and Rh(0) compounds, Ir(I), Ir(III), Ir(IV) and Ir(0) compounds, Ru(II), Ru(III), Ru(IV) and Ru(0) compounds, Pd(II), Pd(IV) and Pd(0) compounds and Pt(II) Pt(IV) and Pt(0) compounds. Preference is given to those transition metal compounds which already have at least one CO ligand. In addition, it is also possible to use transition metal compounds which do not have any CO ligands in the process according to the invention as a starting compound for preparing the catalysts to be used in accordance with the invention. Under the conditions of the preformation which can optionally be carried out in accordance with the invention or the inventive hydrogenation conditions, these are converted to the desired catalysts with addition of carbon monoxide.

Examples of transition metal compounds which can be used in accordance with the invention are: $RhCl_3$, $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$, $Rh_6(CO)_{16}$ or $Ir_4(CO)_{12}$, $[Ir(cod)Cl]_2$, where "acac" is an acetylacetonate ligand and "cod" is a cyclooctadiene ligand.

The transition metal compounds and complexes mentioned and further examples thereof are known and are adequately described in the literature or may be prepared by those skilled in the art analogously to the compounds already known.

According to the invention, the transition metal compounds mentioned are used typically in an amount of from about 0.01 to about 1 mol %, preferably of from about 0.05 to about 0.5 mol %, in particular of from about 0.02 to about 0.2 mol % (based on the transition metal atoms present) in relation to the amount of substrate to be hydrogenated.

In the case of reactions carried out under continuous conditions, the ratio of amount of transition metal compound used as a precursor of the inventive homogeneous catalyst to the amount of substrate to be hydrogenated is advantageously selected in such a way that a catalyst concentration in the range of from about 100 ppm to 10 000 ppm, in particular in the range of from about 200 ppm to 5000 ppm, is maintained.

According to the invention, the transition metal compounds mentioned are contacted with a further compound which is optically active, preferably substantially enantiomerically pure (i.e. has an enantiomeric excess of at least about 99%) and has at least one phosphorus and/or arsenic atom, preferably at least one phosphorus atom. This compound, to be referred to as a chiral ligand, forms the transition metal catalyst to be used in accordance with the invention in the reaction mixture, or in the preformation mixture with the transition metal compound used.

Special preference is given to those chiral ligands which have two phosphorus atoms and form chelate complexes with the transition metal used.

Suitable chiral ligands in the context of the present invention are those compounds as described, for example, in: I. Ojima (ed.), *Catalytic Asymmetric Synthesis*, Wiley-VCh, 2nd edition, 2000 or in E. N. Jacobsen, A. Pfaltz, H. Yamamoto (eds.), *Comprehensive Asymmetric Catalysis*, 2000, Springer, or in W. Tang, X. Zhang, *Chem. Rev.* 2003, 103, 3029-3069.

The following compounds are listed by way of example as chiral ligands which can be used with preference in accordance with the invention:

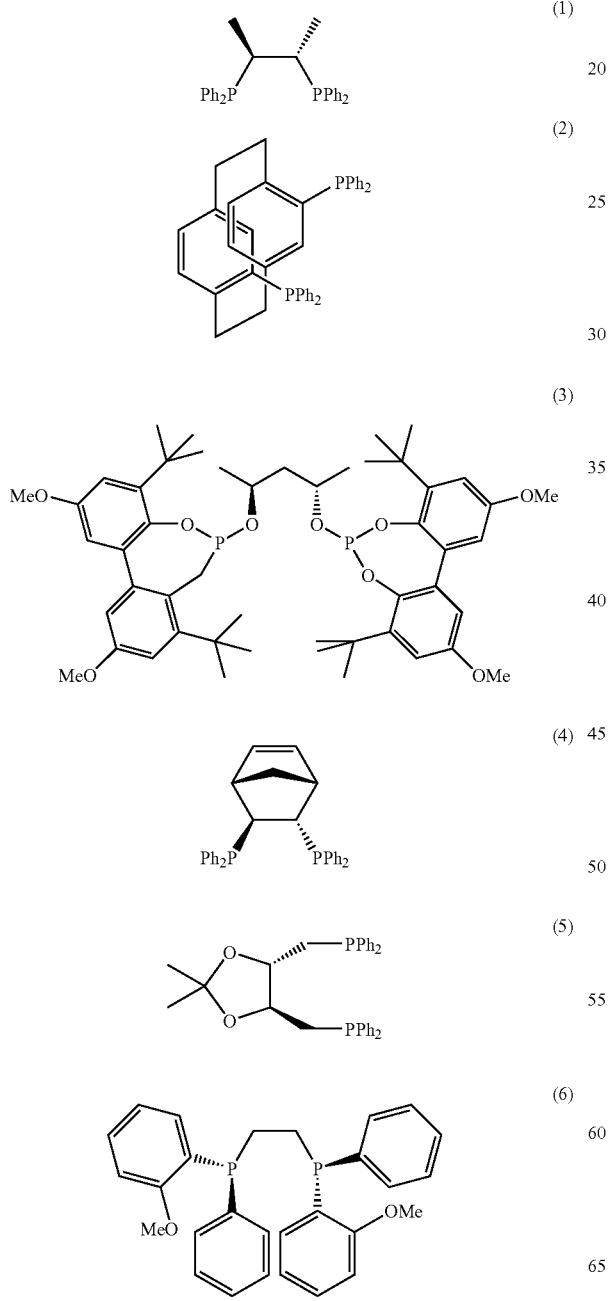

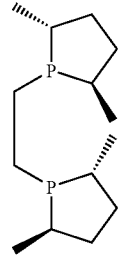

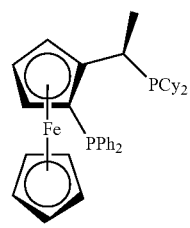

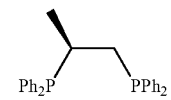

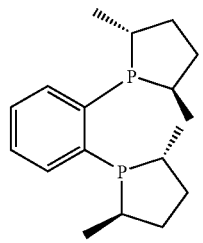

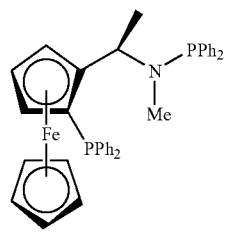

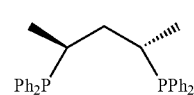

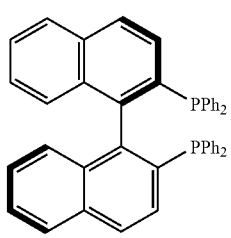

Additionally listed by way of example as chiral ligands which can be used in accordance with the invention are the following compounds:

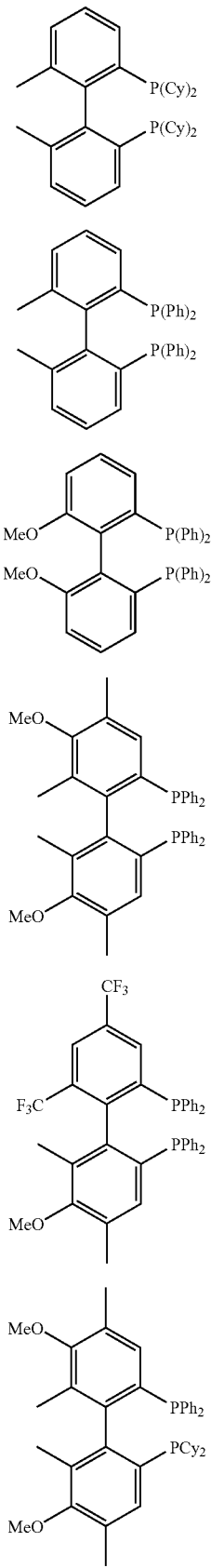
(14)
(15)
(16)
(17)
(18)
(19)
-continued
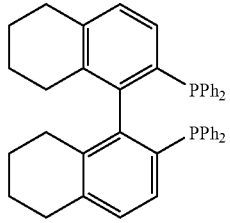
(20)
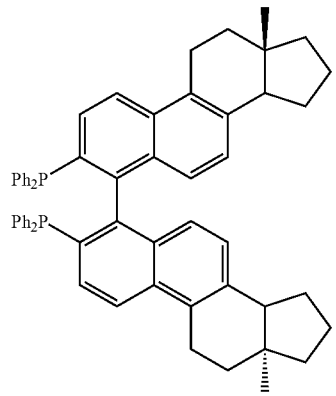
(21)
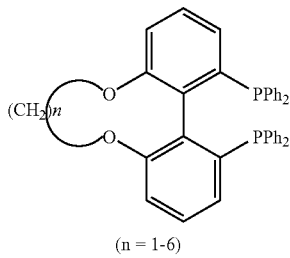
(22)
(n = 1-6)
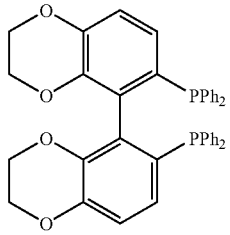
(23)
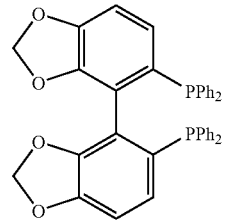
(24)
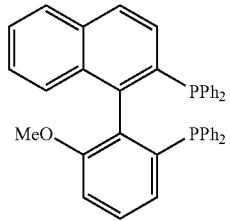
(25)

-continued
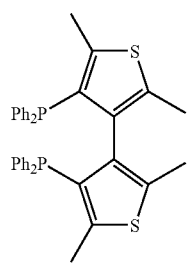 (26)
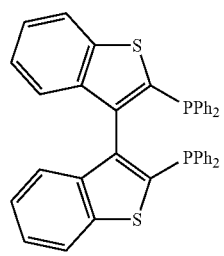 (27)
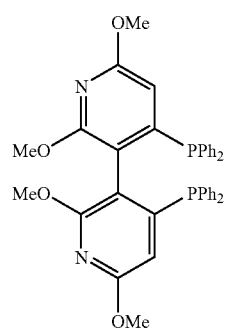 (28)
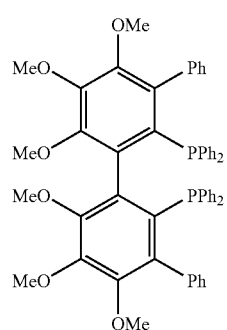 (29)
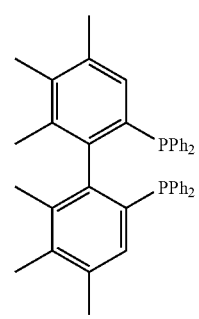 (31)
-continued
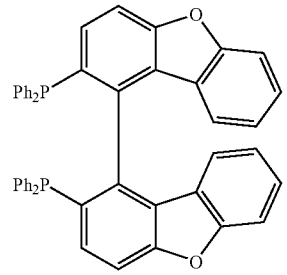 (32)
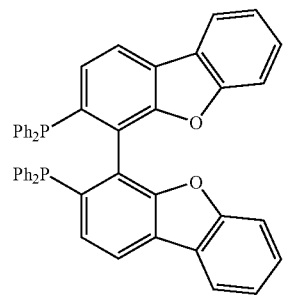 (33)
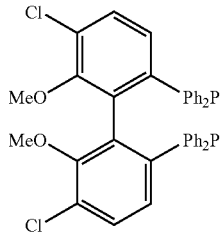 (34)
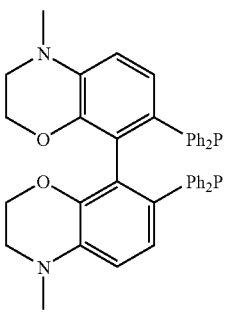 (35)
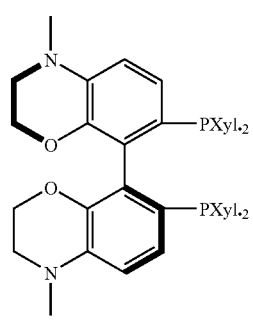 (36)

-continued
(37) 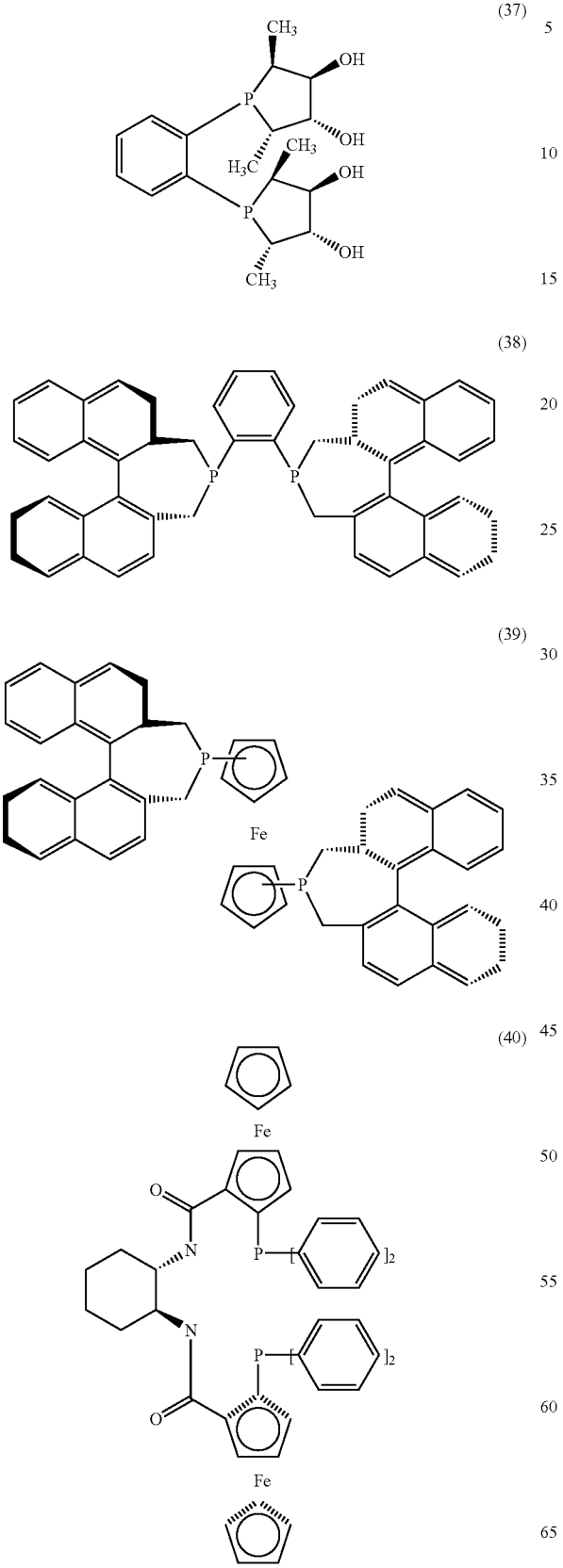
(38)
(39)
(40)
(41) 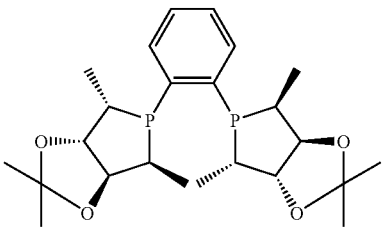
(42) 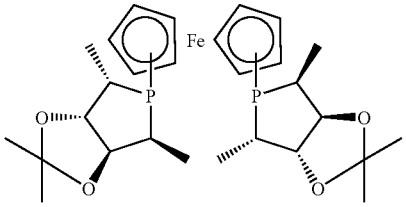
(43) 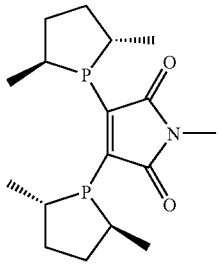
(44) 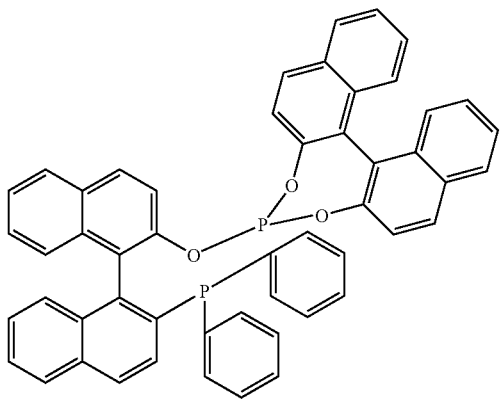
(45) 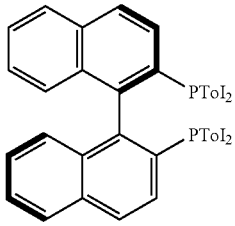
(46) 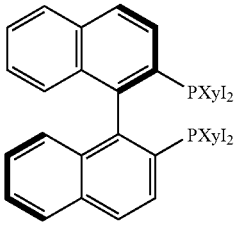

-continued
(47)
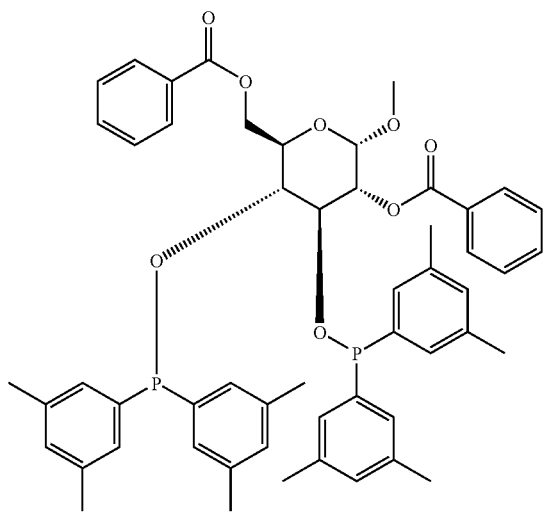
(48)
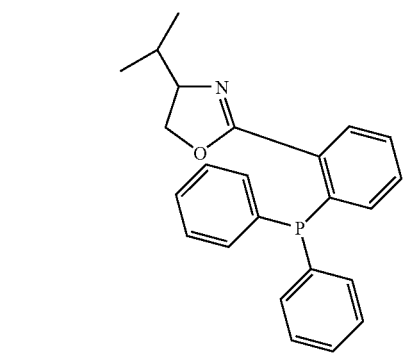
(49)
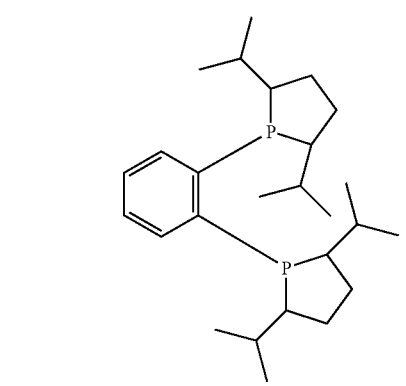
(50)
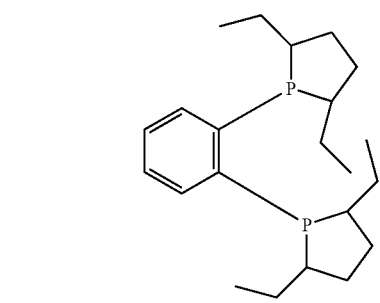
-continued
(51)
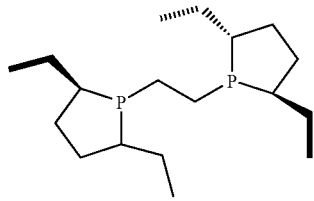
(52)
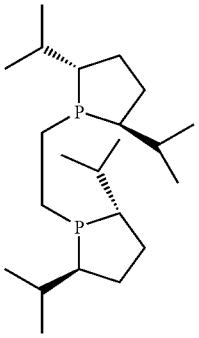
(53)
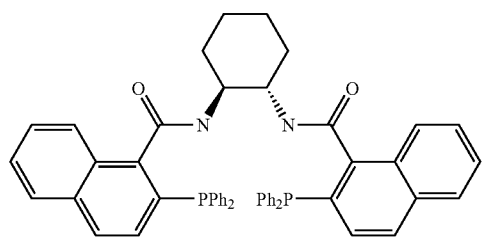
(54)
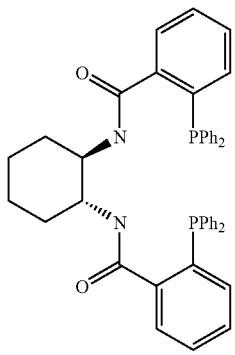
(55)
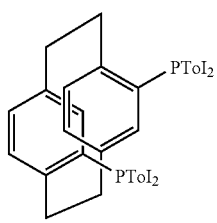
(56)
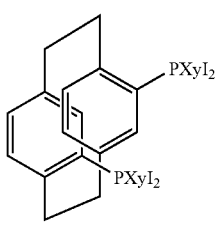

-continued
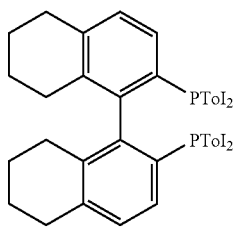
(57)
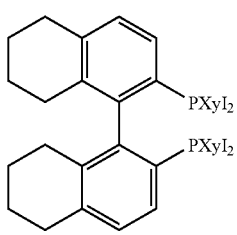
(58)
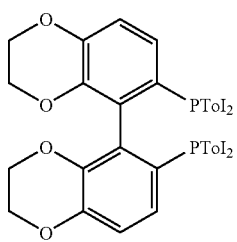
(59)
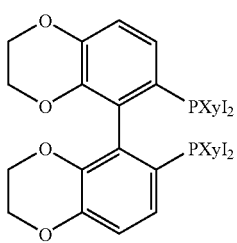
(60)
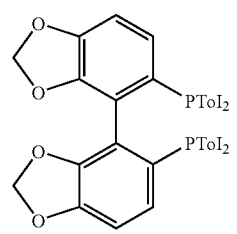
(61)
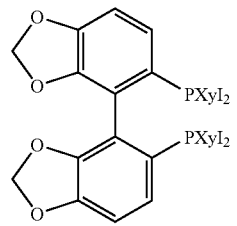
(62)
-continued
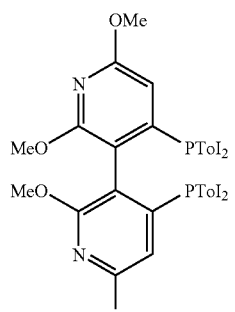
(63)
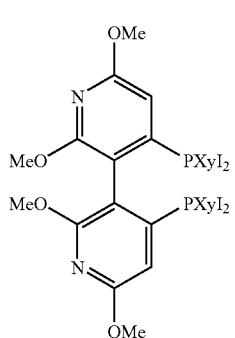
(64)
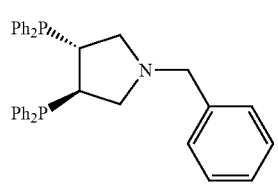
(65)
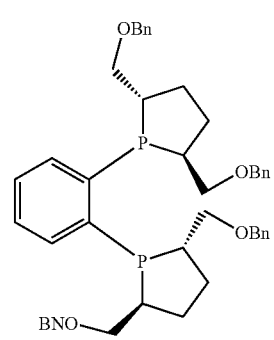
(66)
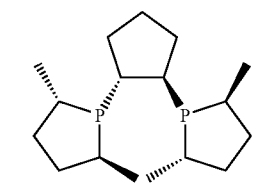
(67)
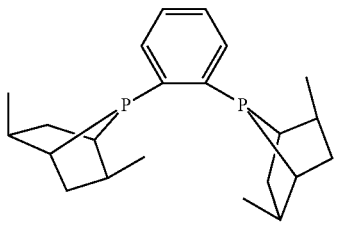
(68)

-continued
(69)
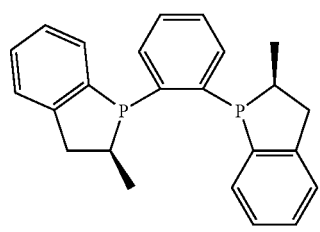
(70)
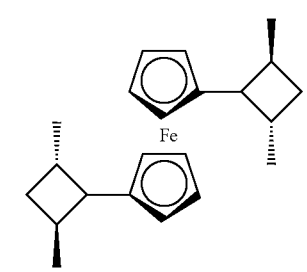
(71)
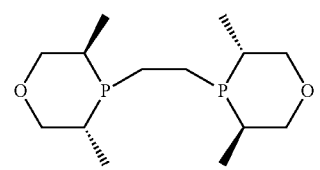
(72)
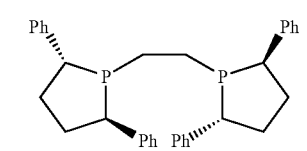
(73)
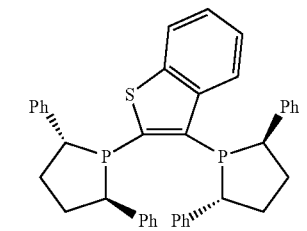
(74)
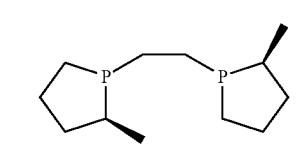
(75)
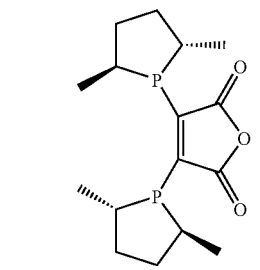
-continued
(76)
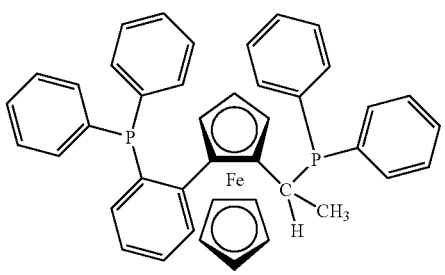
(77)
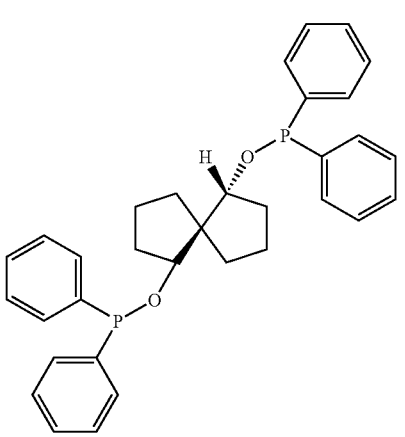
(78)
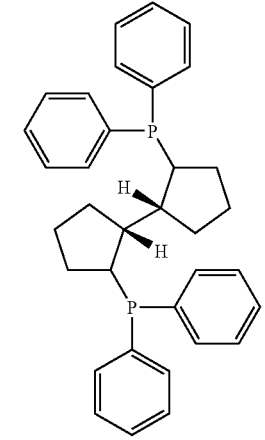
(79)
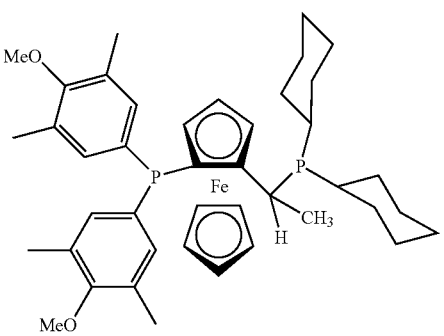

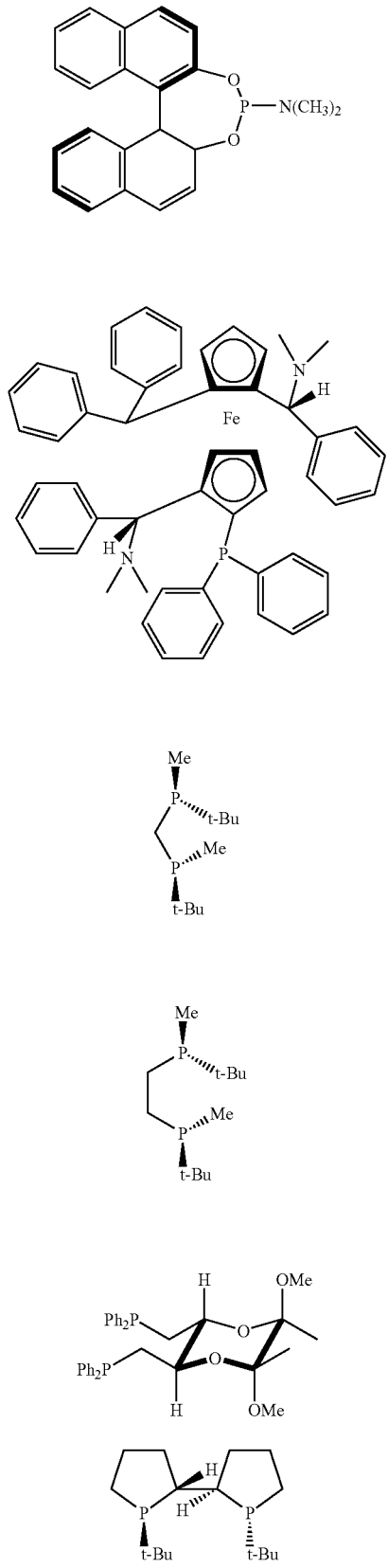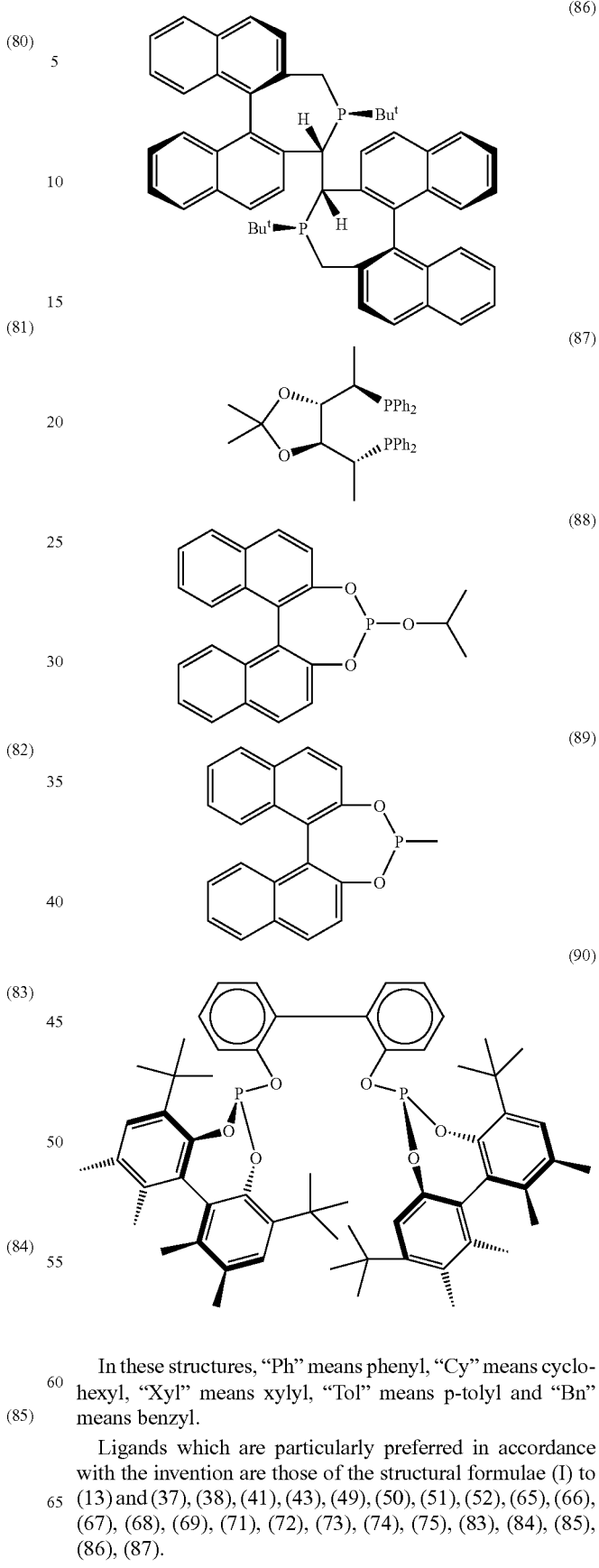
In these structures, "Ph" means phenyl, "Cy" means cyclohexyl, "Xyl" means xylyl, "Tol" means p-tolyl and "Bn" means benzyl.
Ligands which are particularly preferred in accordance with the invention are those of the structural formulae (I) to (13) and (37), (38), (41), (43), (49), (50), (51), (52), (65), (66), (67), (68), (69), (71), (72), (73), (74), (75), (83), (84), (85), (86), (87).

Especially preferred ligands are those of the general formulae (IX) to (XI)

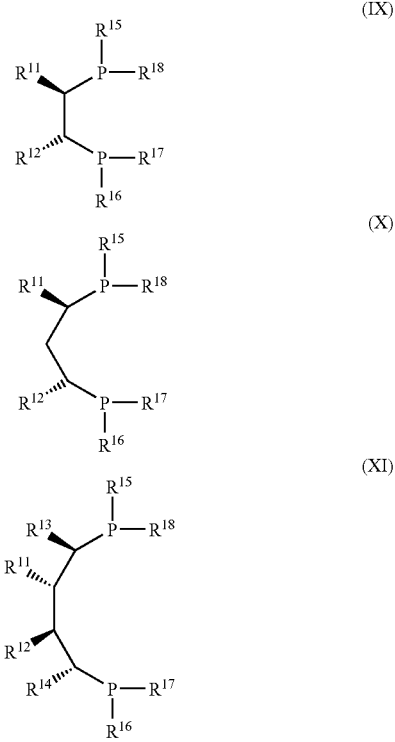

in which

R$^{11}$, R$^{12}$: are each independently an unbranched, branched or cyclic alkyl radical which has from 1 to 20 carbon atoms and may optionally bear one or more, generally from 1 to about 4, ethylenic double bonds and/or one or more, generally from 1 to about 4, identical or different substituents selected from the group of the OR$^{19}$, NR$^{20}$R$^{21}$, halogen, C$_6$-C$_{10}$-aryl and C$_3$-C$_9$-hetaryl substituents, and R$^{11}$ and R$^{12}$ together may form a 4- to 20-membered ring which may contain one or more, generally 1 or 2, oxygen atoms, and R$^{13}$, R$^{14}$: are each independently hydrogen or straight-chain or branched C$_1$- to C$_4$-alkyl, and R$^{15}$, R$^{16}$, R$^{17}$, R$^{18}$: are each C$_6$- to C$_{10}$-aryl, each of which may optionally bear one or more, generally from 1 to 8, preferably from 1 to 4, substituents selected from the group of the C$_1$- to C$_4$-alkyl, C$_6$- to C$_{10}$-aryl, C$_1$- to C$_4$-alkoxy and amino substituents, and R$^{19}$, R$^{20}$, R$^{21}$: are each independently hydrogen, C$_1$-C$_4$-alkyl, C$_6$-C$_{10}$-aryl, C$_7$-C$_{12}$-aralkyl or C$_7$-C$_{12}$-alkylaryl, where R$^{20}$R$^{21}$: together may also be an alkylene chain which has from 2 to 5 carbon atoms and may be interrupted by N or O.

Ligands especially preferred in the process according to the invention are those of the general formula (IX), especially the compounds of the formula (1) referred to hereinafter as "chiraphos".

According to the invention, the chiral ligands selected may each be used in the form of their two enantiomers.

When chiral ligands having two phosphorus atoms are used, they are advantageously used in an amount of from about 1 to about 10 mol, preferably from about 1 to about 4 mol, per mole of transition metal compound used.

The actual precatalysts comprising at least one carbon monoxide ligand may be obtained from the selected transition metal compound and the selected chiral ligand by combining and if appropriate preforming with a mixture of hydrogen and carbon monoxide.

The process according to the invention should be carried out in such a way that the catalyst which is soluble in the reaction mixture, i.e. homogeneous, if desired in the presence of the substrate to be hydrogenated asymmetrically, is either pretreated with a gas mixture which comprises carbon monoxide and hydrogen before the asymmetric hydrogenation (i.e. a preformation of the catalyst is carried out) or the asymmetric hydrogenation is carried out in the presence of carbon monoxide supplied additionally to the reaction mixture or a preformation is carried out and the asymmetric hydrogenation is subsequently carried out in the presence of carbon monoxide supplied additionally to the reaction mixture.

Preference is given to carrying out the process according to the invention in such a way that the catalyst is pretreated with a gas mixture comprising carbon monoxide and hydrogen (i.e. preformed) and the asymmetric hydrogenation is carried out in the presence of carbon monoxide supplied additionally to the reaction mixture.

When a preformation is carried out, the selected transition metal compound and the selected chiral ligands and, if desired, the substrate to be hydrogenated asymmetrically are typically dissolved in a suitable solvent or solution medium which is inert under the reaction conditions, for example ether, tetrahydrofuran, toluene, chlorobenzene, octadecanol, biphenyl ether, Texanol, Marlotherm, Oxo oil 9N (hydroformylation products of isomeric octenes, BASF Aktiengesellschaft) and the like. The solution medium used may also be the substrate to be reacted, the product or any high-boiling by-products which occur in the reaction. A gas mixture which comprises hydrogen and carbon monoxide is injected into the resulting solution, advantageously in a suitable pressure reactor or autoclave, at a pressure of typically from about 5 to about 350 bar, preferably of from about 20 to about 200 bar and more preferably of from about 50 to about 100 bar. For the preformation, preference is given to using a gas mixture which comprises about from 30 to 99% by volume of hydrogen,
from 1 to 70% by volume of carbon monoxide and
from 0 to 5% by volume of further gases, the data in % by volume having to add up to 100% by volume, comprises.

For the preformation, particular preference is given to using a gas mixture which comprises about from 40 to 80% by volume of hydrogen,
from 20 to 60% by volume of carbon monoxide and
from 0 to 5% by volume of further gases, the data in % by volume having to add up to 100% by volume, comprises.

A gas mixture which is especially preferred for the preformation is what is known as synthesis gas which consists typically to an extent of from about 35 to 55% by volume of carbon monoxide as well as hydrogen and traces of further gases.

The inventive preformation of the catalyst is typically carried out at temperatures of from about 25° C. to about 100° C., preferably at from about 40° C. to about 80° C. When the preformation is carried out in the presence of the substrate to be hydrogenated asymmetrically, the temperature is advantageously selected in such a way that it does not result to a troublesome degree in isomerization of the double bond to be hydrogenated. The preformation is complete typically after from about 1 h to about 24 h, often after from about 1 to about 12 h.

After the preformation to be carried out optionally, the asymmetric hydrogenation of the selected substrate is carried out in accordance with the invention. After preceding preformation, the selected substrate can generally be carried out with good success with or without supply of additional carbon monoxide. When a preceding preformation has been dispensed with, the inventive asymmetric hydrogenation should be carried out in the presence of carbon monoxide supplied additionally to the reaction system. Particularly advantageously, a preformation is carried out as described and additional carbon monoxide is supplied to the reaction mixture during the asymmetric hydrogenation.

The addition of additional carbon monoxide may be undertaken in various ways: for example, the carbon monoxide may be added to the hydrogen to be used for the asymmetric hydrogenation or else metered directly into the reaction solution in gaseous form. A further possibility is, for example, to add compounds to the reaction mixture which readily release carbon monoxide, for example formates or oxalyl compounds.

Preference is given to adding carbon monoxide to the hydrogen used for the asymmetric hydrogenation. The proportion of carbon monoxide in the hydrogen used is typically from about 100 to about 10 000 ppm, preferably from about 500 to about 5000 ppm and more preferably from about 600 to about 3000 ppm.

The inventive asymmetric hydrogenation is undertaken advantageously at a pressure of from about 1 to about 300 bar, preferably of from about 10 to about 100 bar, in particular at from about 50 to about 100 bar, and a temperature of generally from about 0° C. to about 100° C. preferably from about 0° C. to about 30° C., in particular at from about 10° C. to about 30° C.

The selection of the solvent to be used to carry out the inventive asymmetric hydrogenation is not critical. Suitable solvents are, for example, those mentioned for the performance of the inventive preformation. Particularly advantageously, the asymmetric hydrogenation is carried out in the same solvent as the preformation carried out beforehand if appropriate.

The process according to the invention may be carded out with good success with and without addition of tertiary amines. Preference is given to carrying out the process according to the invention in the absence, i.e. without addition of additional tertiary amines or in the presence only of catalytic amounts of additional tertiary amines.

Suitable reaction vessels for carrying out the inventive asymmetric hydrogenation are in principle all of those which allow the reactions under the conditions mentioned, in particular pressure and temperature, and are suitable for hydrogenation reactions, for example autoclaves, tubular reactors, bubble columns, etc.

Advantageously, the reaction is terminated when the target compound is present in the reaction mixture in the desired yield and the desired optical activity, i.e. with the desired enantiomeric excess (ee), as can be determined by those skilled in the art by routine analyses, for example by means of chromatographic methods. Typically, the hydrogenation is complete after from about 1 to about 150 h, often after from about 2 to about 24 h.

The process according to the invention succeeds in providing optically active carbonyl compounds, especially optically active aldehydes, in high yields and in enantiomeric excesses. Typically, the desired asymmetrically hydrogenated compounds are obtained in an enantiomeric excess of at least 80% ee, often with an enantiomeric excess of from about 85 to about 99% ee. It should be noted that the maximum achievable enantiomeric excess can depend upon the purity of the substrate used, especially with regard to the isomeric purity of the double bond to be hydrogenated.

Accordingly, suitable starting substances are in particular those which have an isomeric ratio of at least about 90:10, preferably at least about 95:5, with regard to the E/Z double bond isomers.

The process according to the invention is notable in that the homogeneous catalysts used are stabilized by the carbon monoxide introduced additionally into the reaction system, which firstly distinctly increases the lifetime of the catalysts and secondly makes it possible to reuse the homogeneous catalysts.

For example, the resulting reaction product can be removed from the reaction mixture by processes known per se to those skilled in the art, for example by distillation, and the remaining catalyst, if appropriate after repeated preformation, can be utilized in further reactions.

The process according to the invention may accordingly be operated batchwise or semicontinuously or continuously, and is especially suitable for reactions on the industrial scale.

In a particularly preferred embodiment of the process according to the invention, neral or geranial, each of which comprises up to about 5 mol %, preferably up to about 2 mol %, of the particular double bond isomer, is converted to optically active citronellal.

To form the catalyst, preference is given to using a compound of rhodium which is soluble in the reaction mixture, in particular $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$ or $Rh_6(CO)_{16}$, and, as the chiral ligand, (R,R)-chiraphos or (S,S)-chiraphos ((2R,3R)-(+)-2,3-bis(diphenylphosphino)butane and (2S,3S)-(−)-2,3-bis(diphenylphosphino)butane respectively) in a molar ratio of from about 1:1 to about 1:4. In an especially preferred embodiment of the process according to the invention, neral which comprises up to about 5 mol %, preferably up to about 2 mol % of geranial is converted in the presence of $Rh(OAc)_3$, $[Rh(cod)Cl]_2$, $Rh(CO)_2acac$, $[Rh(cod)OH]_2$, $[Rh(cod)OMe]_2$, $Rh_4(CO)_{12}$ or $Rh_6(CO)_{16}$ and (R,R)-chiraphos to D-citronellal. Preference is given to preforming the catalyst under the conditions mentioned above and to subsequently carrying out the asymmetric hydrogenation in the presence of hydrogen which comprises from about 600 to about 3000 ppm of carbon monoxide. In the preferred embodiment, the addition of solvents is advantageously dispensed with and the reactions mentioned are carried out in the substrate to be converted or the product and if appropriate in high-boiling by-products as a solution medium. Special preference is given to a continuous reaction with reuse or recycling of the homogeneous catalyst stabilized in accordance with the invention.

A further aspect of the present invention relates to a process for preparing optically active menthol using optically active citronellal prepared by the process according to the invention. The preparation of optically active menthol starting from optically active citronellal is known. A key step in this context is the cyclization of optically active citronellal to optically active isopulegol, as described, for example, in EP-A 1 225 163.

The optically active citronellal prepared in accordance with the invention can, as shown schematically below for the preparation of L-menthol of the formula (XIII), be cyclized in the presence of a suitable acid, in particular of a Lewis acid, to give L-isopulegol of the formula (XII), and subsequently be hydrogenated to give L-menthol.

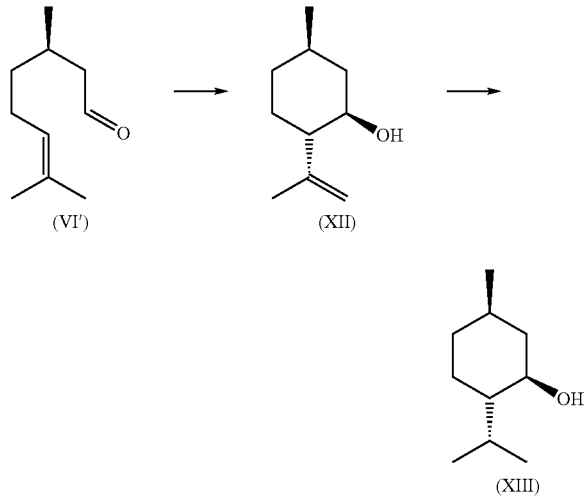

A further aspect of the present invention accordingly relates to the use of optically active citronellal prepared by the process according to the invention for preparing optically active menthol. In particular, the invention relates to the use of D-citronellal prepared by the process according to the invention for preparing optically active L-menthol.

The examples which follow serve to illustrate the invention without compromising it in any way:

EXAMPLE 1

Asymmetric Hydrogenation of Cis-citral in the Presence of Carbon Monoxide 17.9 mg of $Rh(CO)_2$acac and 38.5 mg of (R,R)-chiraphos were dissolved in 20 g of toluene under a protective gas atmosphere and transferred to a 100 ml autoclave which had been purged beforehand 3 times with a mixture of carbon monoxide and hydrogen (1:1, vol./vol.). The mixture was stirred at a 1:1 $CO/H_2$ pressure of 8 bar and 60° C. for 3 h and subsequently cooled to room temperature. By means of a pressure lock, 10.94 g of neral (ratio of the neral/geranial double bond isomers=99.1:0.9; substrate/catalyst ratio=1000) were then injected with 15 bar of $H_2$. The reaction pressure was adjusted to 80 bar by injecting hydrogen. To reduce the partial CO pressure, the pressure was lowered three times to 8 bar and restored three times to 80 bar by injecting hydrogen, and, after 3 h, lowered to 8 bar once more. After 18 h, gas chromatography was used to determine a conversion of 99.9% and a yield of D-citronellal of 99.8% with an optical purity of 90% ee.

EXAMPLE 2

Asymmetric Hydrogenation of Neral in the Presence of Carbon Monoxide 17.0 mg of $Rh(CO)_2$acac and 43.8 mg of (R,R)-chiraphos were dissolved in 0.8 ml of THF and stirred in an autoclave at 80 bar of synthesis gas ($H_2$/CO=1:1, vol./vol.) and 60° C. for 8 h. Subsequently, 39.00 g of neral (ratio of the neral/geranial double bond isomers=95.2:4.8; substrate/catalyst ratio=4000) were dissolved and introduced together with the catalyst solution into a 100 ml autoclave which had been purged 3 times with 1:1 $CO/H_2$ (vol./vol.) beforehand. The reaction pressure was adjusted to 80 bar by injecting hydrogen gas which comprised 1000 ppm of carbon monoxide. After 144 h, a conversion of 84.3% and a yield of 80.9% of D-citronellal having an optical purity of 64% ee was determined by gas chromatography.

EXAMPLE 3

Asymmetric Hydrogenation of Neral with Reuse of the Catalyst 23.7 mg of $Rh(CO)_2$acac and 55.7 mg of (R,R)-chiraphos were dissolved in 24 g of THF under a protective gas atmosphere and introduced into a 100 ml autoclave which had been purged 3 times with 1:1 $CO/H_2$ (vol./vol.) beforehand. The mixture was stirred at a 1:1 $CO/H_2$ pressure of 80 bar and 60° C. for 3 h. Subsequently, the mixture was cooled to room temperature and decompressed to a pressure of 8 bar of 1:1 $CO/H_2$. By means of a pressure lock, 13.2 g of neral (ratio of the neral/geranial double bond isomers=99.4:0.6) were injected with 15 bar of $H_2$. The reaction pressure was adjusted to 80 bar by injecting hydrogen. To reduce the partial CO pressure, the pressure was lowered 5 times to 8 bar and restored 5 times to 80 bar by injecting hydrogen. The content, determined by gas chromatography, of CO in the headspace was 510 ppm. After in each case 20 h and 40 h, a further 13.20 g and 19.80 g, respectively, of neral were added. After 66 h, a conversion of 75.8% and a yield of 72.8% of D-citronellal with an optical purity of 87% ee was determined by gas chromatography.

The overall turnover number based on the yield of D-citronellal was 1030.

EXAMPLE 4

Asymmetric Hydrogenation of Cis-citral while Distilling Off the Product and Reusing the Catalyst 8.4 mg of $Rh(CO)_2$acac and 21.6 mg of (R,R)-chiraphos were dissolved in 0.8 ml of THF and stirred in an autoclave at 80 bar of synthesis gas ($H_2$/CO=1:1, vol./vol.) and 60° C. for 8 h. Afterward, 9 g of neral (ratio of the neral/geranial double bond isomers=95.2:4.8) were introduced into the autoclave. The reaction pressure was adjusted to 80 bar by injecting hydrogen gas which comprised 1000 ppm of carbon monoxide. After 24 h, a conversion of 99% had been attained; the ee of the resulting D-citronellal was 83%.

After the product had been distilled off, a further 8.5 g of neral (ratio of the neral/geranial double bond isomers=95.2:4.8) were added and hydrogenation was effected at 80 bar of hydrogen gas which comprised 1000 ppm of carbon monoxide for 48 h. The conversion was 36%, the ee of the resulting D-citronellal was 54%.

After the product had been distilled off once again, a further 6.8 g of neral (ratio of the neral/geranial double bond isomers=95.2:4.8) were added and hydrogenation was effected at 80 bar of hydrogen gas which comprised 1000 ppm of carbon monoxide for 72 h. The conversion was 13%, the ee of the resulting D-citronellal was 30%.

The overall turnover number based on the yield of D-citronellal was 2312.

EXAMPLE 5

Asymmetric Hydrogenation of Neral with Preformation, Removal of the Product and Reuse of the Catalyst 30 mg of $Rh(CO)_2acac$ and 75 mg of (R,R)-chiraphos were dissolved in 3 ml of THF and stirred in an autoclave at 60° C. in the presence of 80 bar of synthesis gas ($H_2/CO=1:1$, vol./vol) for 20 h. Subsequently, 37 g of neral (ratio of the neral/geranial double bond isomers=96.6:3.4) were added and the solution was introduced into a 100 ml autoclave which had been purged beforehand 3 times with 1:1 $CO/H_2$ (vol./vol.). The reaction pressure was adjusted to 80 bar by injecting hydrogen gas which comprises 1000 ppm of carbon monoxide. After 24 h, a conversion of >99% had been attained; the ee of the resulting D-citronellal was 87%.

After the product had been distilled off, the distillation residue was diluted with THF and stirred in an autoclave at 60° C. in the presence of synthesis gas ($H_2/CO=1:1$) at a pressure of 80 bar for 20 h. Afterward, a further 32 g of neral (ratio of the neral/geranial double bond isomers=96.6:3.4) were added and hydrogenation was effected at a pressure of 80 bar of hydrogen gas which comprised 1000 ppm of carbon monoxide for 24 h. The conversion was >99%; the ee of the resulting D-citronellal was 87%.

After the product had been distilled off once again, the distillation residue was diluted with THF and stirred in an autoclave at 60° C. in the presence of 80 bar of synthesis gas ($H_2/CO=1:1$) for 20 h. Afterward, a further 32.96 g of neral (ratio of the neral/geranial double bond isomers=96.6:3.4) were added and hydrogenation was effected at a pressure of 80 bar of hydrogen gas which comprised 1000 ppm of carbon monoxide for 24 h. The conversion was 90%; the optical purity of the resulting D-citronellal was 88% ee.

The experiment was repeated once again with addition of 33 g of neral (ratio of the neral/geranial double bond isomers=96.6:3.4). At a conversion of 17%, D-citronellal was obtained with an optical purity of 89% ee.

The overall turnover number based on the overall yield of D-citronellal was 4975.

EXAMPLE 6

Continuous Asymmetric Hydrogenation of Neral

In a continuous laboratory apparatus, a solution of 2.13 g of $Rh(CO)_2acac$ and 6.00 g of (R,R)-chiraphos in 70 g of THF and 60 g of Oxo oil 9N (BASF Aktiengesellschaft) which had been stirred beforehand for 20 h at 60° C. and a 1:1 $CO/H_2$ (vol./vol.) pressure of 80 bar and 170 g of neral (ratio of the neral/geranial double bond isomers approx. 95:5) were introduced, and the gas mixture in the preformation reactor of the apparatus was then adjusted to 10 000 ppm of carbon monoxide in hydrogen (80 bar), and the temperature to 60° C. In the hydrogenation reactor, a gas mixture of 1000 ppm of carbon monoxide in hydrogen (80 bar) and a temperature of 25° C. was established.

The feed of fresh reactant was adjusted to 6 g/h. A product-containing fraction was distilled off continuously under reduced pressure in such a way that the apparatus contents remain virtually constant. In the course of 19 days, 6.01 mol (927.7 g) of D-citronellal were obtained. The overall turnover number based on the yield of D-citronellal is 10914.

EXAMPLE 7

Asymmetric Hydrogenation of 3-methylcyclopent-2-enone in the Presence of Carbon Monoxide 0.3049 g of $Rh(CO)_2acac$ and 0.7767 g of (R,R)-chiraphos were dissolved in 15 g of tetrahydrofuran under a protective gas atmosphere and transferred into a 100 ml autoclave which had been purged 3 times beforehand with a mixture of carbon monoxide and water (1:1, vol./vol.). It was stirred at a pressure of 8 bar of 1:1 $CO/H_2$ and 60° C. for 24 h and then cooled to room temperature. 2.48 g were withdrawn under a protective gas atmosphere from the resulting stock solution and dissolved in 35 ml of tetrahydrofuran. By means of a syringe, 2.0 g of 3-methylcyclopent-2-enone were added, and the mixture was stirred at 50° C. and 60 bar of hydrogen gas comprising 2000 ppm of carbon monoxide for 21 h. The conversion to 3-methylcyclopentanone was 99%; the enantiomeric excess was 87%.

COMPARATIVE EXAMPLE 1

Asymmetric Hydrogenation of Neral 12.3 mg of $Rh_4(CO)_{12}$ and 31.5 mg of (S,S)-chiraphos were dissolved in 15 g of toluene under a protective gas atmosphere and transferred to a 100 ml autoclave which had been purged beforehand 3 times with $H_2$. The mixture was stirred at 1.5 bar of $H_2$ for 1.5 h and decompressed to standard pressure, and 1 g of neral (ratio of the neral/geranial double bond isomers=98.7:1.3; substrate/catalyst ratio=100) dissolved in 15 g of toluene was added by means of a syringe. The reaction pressure was adjusted to 90 bar by injecting hydrogen. Gas chromatography reaction monitoring showed full conversion after 15 h and a yield, determined by gas chromatography, of 98% L-citronellal having an optical purity of 96% ee.

What is claimed is:

1. A process for preparing optically active carbonyl compounds which comprises asymmetrically hydrogenating α,β-unsaturated carbonyl compounds in the presence of optically active transition metal catalysts which are soluble in the reaction mixture and have at least one carbon monoxide ligand, and pretreating the catalyst with a gas mixture comprising carbon monoxide and hydrogen and/or carrying out the asymmetric hydrogenation in the presence of carbon monoxide supplied additionally to the reaction mixture.

2. The process according to claim 1, wherein the optically active carbonyl compounds are of the formula (I)

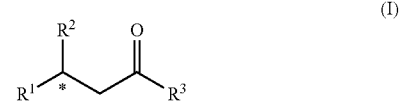

wherein
the $R^1$ and $R^2$ radicals are each an unbranched, branched or cyclic alkyl radical which has from 1 to 25 carbon atoms and may optionally bear one or more ethylenic double bonds and/or one or more identical or different substituents selected from the group of the $OR^4$, $NR^5R^6$, halogen, $C_6$-$C_{10}$-aryl and $C_3$-$C_9$-hetaryl substituents and which, together with R³, optionally form a 5- to 25-membered ring, with the proviso that R¹ and R² are different, the R³ radical is hydrogen or an unbranched, branched or cyclic alkyl radical which has from 1 to 25 carbon atoms and may optionally bear one or more ethylenic double bonds and/or one or more identical or different substituents selected from the group of the OR⁴, NR⁵R⁶, halogen, $C_6$-$C_{10}$-aryl and $C_3$-$C_9$-hetaryl substituents, or is OR⁷ or NR⁸R⁹, where R⁴, R⁵ and R⁶ are each independently hydrogen, $C_1$-$C_6$-alkyl, $C_6$-$C_{10}$-aryl, $C_7$$C_{12}$-aralkyl or $C_7$-$C_{12}$-alkylaryl and R⁵ and R⁶ together may also be an alkylene chain having from 2 to 5 carbon atoms which is optionally interrupted by N or O and R⁷ and R⁸ are each an unbranched, branched or cyclic alkyl radical which has from 1 to 25 carbon atoms and may optionally bear one or more ethylenic double bonds and one or more identical or different substituents selected from the group of the OR⁴, NR⁵R⁶, halogen, $C_6$-$C_{10}$-aryl and $C_3$-$C_9$-hetaryl substituents, and, together with R¹ or R², may form a 5- to 25-membered ring and R⁹ is hydrogen, $C_1$-$C_6$-alkyl, $C_6$-$C_{10}$-aryl, $C_7$-$C_{12}$-aralkyl or $C_7$-$C_{12}$-alkylaryl and

* indicates an asymmetric carbon atom, and the process comprises asymmetrically hydrogenating α,β-unsaturated aldehydes or ketones of the formula (II)

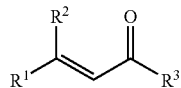
(II)

wherein the R¹ to R³ radicals are each as defined above.

3. The process according to claim 2 for preparing optically active aldehydes or ketones by asymmetrically hydrogenating α,β-unsaturated aldehydes or ketones.

4. The process according to claim 3 for preparing optically active aldehydes of the formula (III)

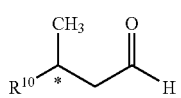
(III)

wherein

R¹⁰ is an unbranched or branched alkyl radical which has from 2 to 25 carbon atoms and may optionally have from 1 to 5 ethylenic double bonds and

* indicates an asymmetric carbon atom, by asymmetrically hydrogenating α,β-unsaturated aldehydes of the formula (IV) or (V)

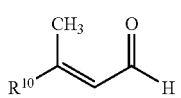
(IV)

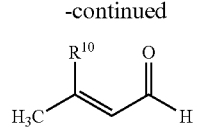
(V)

where the R¹⁰ radical is as defined above.

5. The process according to claim 4 for preparing optically active citronellal of the formula (VI)

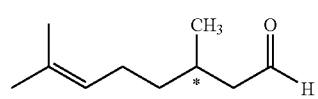
(VI)

by asymmetrically hydrogenating neral of the formula (VII) or geranial of the formula (VIII)

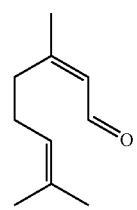
(VII)

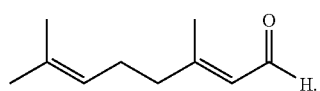
(VIII)

6. The process according to claim 5 for preparing D-citronellal by asymmetrically hydrogenating neral.

7. The process according to claim 2, wherein a transition metal catalyst is used which is obtainable by reaction of at least one transition metal compound soluble in the reaction mixture with an optically active ligand which has at least one phosphorus and/or arsenic atom.

8. The process according to claim 7, wherein the optically active ligand used is of the general formulae (IX), (X) or (XI)

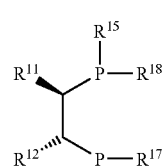
(IX)

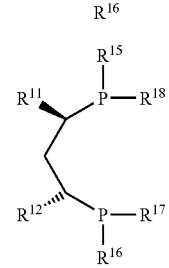
(X)

-continued

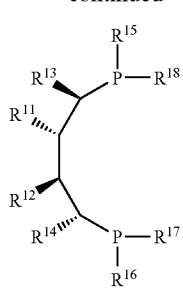

(XI)

in which

R$^{11}$ and R$^{12}$: are each independently an unbranched, branched or cyclic alkyl radical which has from 1 to 20 carbon atoms and may optionally bear one or more ethylenic double bonds and/or one or more identical or different substituents selected from the group of the OR$^{19}$, NR$^{20}$R$^{21}$, halogen, C$_6$-C$_{10}$-aryl and C$_3$-C$_9$-hetaryl substituents, and R$^{11}$ and R$^{12}$ together may form a 4- to 20-membered ring which optionally contains one or more oxygen atoms, and R$^{13}$ and R$^{14}$: are each independently hydrogen or straight-chain or branched C$_1$- to C$_4$-alkyl, and R$^{15}$, R$^{16}$, R$^{17}$ and R$^{18}$: are each C$_6$- to C$_{10}$-aryl, each of which may optionally bear one or more substituents selected from the group consisting of C$_1$- to C$_4$-alkyl, C$_6$- to C$_{10}$-aryl, C$_1$- to C$_4$-alkoxy and amino substituents, and R$^{19}$, R$^{20}$ and R$^{21}$: are each independently hydrogen, C$_1$-C$_4$-alkyl, C$_6$-C$_{10}$-aryl, C$_7$-C$_{12}$-Aralkyl or C$_7$-C$_{12}$-alkylaryl, where R$^{20}$ and R$^{21}$: together may also be an alkylene chain which has from 2 to 5 carbon atoms and may be interrupted by N or O).

9. The process according to claim 7, wherein the transition metal compound is a compound of a metal of transition group VIII of the Periodic Table of the Elements.

10. The process according to claim 7, wherein a compound of the metals rhodium or iridium is used.

11. The process according to claim 7, wherein an optically active ligand is used which comprises two phosphorus atoms.

12. The process according to claim 1, wherein the catalyst is pretreated with a gas mixture comprising carbon monoxide and hydrogen, and the asymmetric hydrogenation is carried out in the presence of carbon monoxide supplied additionally to the reaction mixture.

13. The process according to claim 1, wherein the catalyst is pretreated with a gas mixture which comprises
from 30 to 99% by volume of hydrogen,
from 1 to 70% by volume of carbon monoxide and
from 0 to 5% by volume of further gases,
the data in % by volume having to add up to 100% by volume.

14. The process according to claim 1, wherein hydrogen which comprises from 100 to 10 000 ppm of carbon monoxide is used for the asymmetric hydrogenation.

15. The process according to claim 1, wherein the asymmetric hydrogenation is carried out at a pressure of from 10 to 100 bar.

16. The process according to claim 1, which is carried out continuously.

17. A process for preparing optically active menthol using optically active citronellal prepared according to claim 6.

18. The process according to claim 17, wherein optically active citronellal prepared according to claim 6 is cyclized in the presence of a Lewis acid to give L-isopulegol and subsequently hydrogenated.

19. A process for preparing optically active menthol, comprising the steps of
a) preparing optically active citronellal according to claim 6,
b) cyclizing the optically active citronellal obtained in step a) to give optically active isopulegol and
c) hydrogenating the optically active isopulegol obtained in step b) to give optically active menthol.

20. The process according to claim 8, wherein
R$^{11}$ and R$^{12}$ are each independently an unbranched, branched or cyclic alkyl radical which has from 1 to 20 carbon atoms and may optionally bear 1 to about 4, ethylenic double bonds and/or from 1 to about 4, identical or different substituents selected from the group of the OR$^9$, NR$^{20}$R$^{21}$, halogen, C$_6$-C$_{10}$-aryl and C$_3$-C$_9$-hetaryl substituents, and R$^{11}$ and R$^{12}$ together may form a 4- to 20-membered ring which may contain 1 or 2, oxygen atoms, and
R$^{15}$, R$^{16}$, R$^{17}$ and R$^{18}$ are each C$_6$- to C$_{10}$-aryl, each of which may optionally bear from 1 to 4 substituents selected from the group of the C$_1$- to C$_4$-alkyl, C$_6$- to C$_{10}$-aryl, C$_1$- to C$_4$-alkoxy and amino substituents.

* * * * *